United States Patent [19]
Leavitt et al.

[11] Patent Number: 5,741,706
[45] Date of Patent: Apr. 21, 1998

[54] ANTI-HIV RIBOZYMES

[75] Inventors: Markley C. Leavitt; Richard Tritz; Elizabeth Duarte; Jack Barber; Mang Yu, all of San Diego, Calif.

[73] Assignee: Immusol, Incorporated, San Diego, Calif.

[21] Appl. No.: 719,593

[22] Filed: Sep. 25, 1996

Related U.S. Application Data

[60] Provisional application No. 60/020,484 Jun. 13, 1996.
[51] Int. Cl.$^6$ .............................. C12N 15/85; C12Q 1/68
[52] U.S. Cl. .......................... 435/372; 435/6; 435/91.31; 435/172.3; 435/320.1; 435/325; 435/366; 536/23.1; 536/23.2; 536/24.5
[58] Field of Search ..................... 435/6, 91.31, 42.3, 435/320.1, 240.2; 536/23.1, 23.2, 24.5; 514/44

[56] References Cited

U.S. PATENT DOCUMENTS 5,527,895  6/1996  Hampel et al. ................... 536/23.2

FOREIGN PATENT DOCUMENTS

WO 94/26877  11/1994  WIPO.

OTHER PUBLICATIONS

Buzayan, et al., Nature, Non–Enzymatic Cleavage and Litigation of RNAs Complementary to a Plant Virus Satellite RNA, 323:349–352 (1986).

Gerlach, et al. (1986) Virology, Satellite Tobacco Ringspot Virus RNA: Biological Activity of DNA Clones and Their *in Vitro* Transcripts, 151:172–185.

Hampel, et al. (1989) Biochemistry, RNA Catalytic Properties of the Minimum (–)s TRSV Sequence, 28:4929–4933.

Gerlach, et al. (1989) Gene, Sequences Required for Self–Catalysed Cleavage of the Satellite RNA of Tobacco Ringspot Virus, 82:43–52.

Feldstein, et al. (1989) Gene, , Two Sequences Participating in the Autolytic Processing of Satellite Tobacco Ringspot Virus Complementary RNA, 82:53–61.

Yu, et al., Proc. Natl. Acad. Sci. USA (1993), A Hairpin Ribozyme Inhibits Expression of Diverse Strains of Human Immunodeficiency Virus Type 1, 90:6340–6344.

Yamada, et al., Virology (1994), Activity and Cleavage Site Specificty of an Anti–HIV–1 Hairpin Ribozyme in Human T Cells, 205:121–126.

Yamada, et al., Gene Therapy (1994), Intracellular Immunization of Human T Cells with a Hairpin Ribozyme Against Human Immunodeficiency Virus Type 1, 1:38–45.

Yu, et al., Virology (1995), *In Vitro* and *in Vivo* Characterization of a Second Functional Hairpin Ribozyme Against HIV–1, 206:381–386.

Yu, et al. (1995) Proc. Natl. Acad. Sci. USA, Intracellular Immunization of Human Fetal Cord Blood Stem/Progenitor Cells with a Ribozyme Against Human Immunodeficiency Virus Type 1, 92:699–703.

Leavitt, et al., Hum. Gene Ther. (1994), Transfer of an Anti–HIV–1 Ribozyme Gene into Primary Human Lymphocytes, 5:1115–1120.

Barinag, Science 262 : 1512–1514 (1993).

Stull et al. Pharm. Res. 12:465–483 (1995).

Sokol et al. Transgenic Research 5 : 343–371 (1996).

*Primary Examiner*—John Le Guyder
*Attorney, Agent, or Firm*—Townsend and Townsend and Crew LLP

[57] ABSTRACT

GUC and GUA ribozymes which cleave HIV RNA are provided. The ribozymes cleave HIV RNA in vitro and in vivo. When the ribozymes are expressed in cells, they inhibit HIV replication in the cells.

20 Claims, 3 Drawing Sheets

ANTI-HIV RIBOZYMES

This application claims benefit of U.S. Provisional application Ser. No. 60/020,084, filed Jun. 13, 1996.

BACKGROUND OF THE INVENTION

Hairpin ribozymes are catalytic RNA molecules with RNA endonuclease activity. The hairpin ribozyme was originally derived from the 359 bases of the negative strand of the satellite RNA of tobacco ringspot virus. The hairpin ribozyme is catalytic, cleaving target RNA to produce a 5' fragment terminating in a 2',3' cyclic phosphate and a 3' fragment bearing a newly formed Y—OH. The reaction is reversible, forming a normal phosphodiester bond. See generally, Buzayan, et al. *Nature*, 323:349–352 (1986); Gerlach, et al, (1986) *Virology*, 151:172–185; Hampel et al (1989) *Biochemistry*, 28:4929–4933; Gerlach et al., (1989) *Gene*, 82:43–52; Feldstein et al., (1989) *Gene*, 82:53–61; and Hampel et al. Australian Patent No. AU-B-41594/89.

The use of the hairpin ribozyme as an RNA endonuclease has many applications. For instance, the hairpin ribozyme can be used as a general tool for engineering RNA molecules prior to reverse transcription and cloning, in a manner similar to the DNA endonuclease "restriction" enzymes.

More importantly, the hairpin ribozyme is a powerful tool in various cell transduction and gene therapy procedures. For instance, hairpin ribozymes which cleave a particular RNA target sequence can be expressed in cells to prevent expression and translation of RNA molecules comprising the target sequence. Expression of hairpin ribozymes which specifically cleave human immunodeficiency (HIV) RNAs prevent replication of the virus in cells. See, Yu et al., *Proc Natl. Acad. Sci. USA* (1993) 90:6340–6344; Yamada et al., *Virology* (1994) 205:121–126; Yamada et al., *Gene Therapy* (1994) 1:38–45;; Yu et al, *Virology* (1995) 206:381–386; Yu et al. (1995) *PNAS* 92:699–703; and Wong-Staal et al. WO 94/26877 (PCT/US94/05700).

This strategy of expressing ribozymes which cleave an infectious target in a cell is generally referred to as "intracellular immunization." In one case of intracellular immunization, an anti-U5 ribozyme which targets a highly conserved region of the HIV-1 genome protected primary lymphocytes and stem-cell derived macrophage against HIV-1 strains (Leavitt et al., *Hum. Gene Ther.* (1994) 5:1115–1120; Yu et al., *Proc. Natl. Acad. Sci. USA* (1995) 92:699–703).

Ribozyme therapeutic agents are of increasing importance in the treatment and prevention of HIV infection. Ribozymes may be particularly potent therapeutic agents because (i) as RNA molecules, they do not induce host immunity that eliminates cells which express the ribozyme; (ii) although they resemble antisense molecules in their sequence specific recognition of target RNA, their ability to cleave the target RNA catalytically renders them much more efficient than simple anti-sense molecules; and (iii) they can potentially cleave both afferent and efferent viral RNA, and therefore inhibit both preintegration and postintegration steps of the virus replication cycle.

SUMMARY OF THE INVENTION

New catalytic hairpin ribozymes and the nucleic acids encoding the ribozymes are described. The nucleic acids encoding the ribozymes (endo-ribonuclease nucleic acids) are RNA or DNA molecules encoding the ribozymes, or are themselves the ribozyme RNAs. The nucleic acids are optionally present in an expression cassette, where they are operably linked to a promoter to direct expression of the encoded ribozyme. A preferred promoter is a constitutive t-RNA pol III promoter, e.g., similar to a promoter which directs expression of a naturally occurring t-RNA gene.

The invention further provides target sequences for ribozyme cleavage. Ribozymes recognize the target sequences located in nucleic acids encoded, e.g., by the HIV genome. Cleavage of these targets inhibits HIV replication. In addition to HIV, the sequences are optionally present in naturally occurring or artificial RNAs, which are also cleaved by the ribozymes. The target sequences are RNAs comprising GUC or GUA subsequences. The ribozymes cleave the target sequences in vitro and in vivo.

Because the ribozymes cleave HIV RNAs in vivo, the invention provides a method of inhibiting the replication of HIV in a cell. In the methods of the invention, a nucleic acid encoding a ribozyme of the invention is transduced into a cell. The cell expresses the ribozyme, which inhibits replication of the HIV by cleaving HIV RNAs encoding proteins which aid in the replication of the virus. Targets for this purpose include, but are not limited to,. RNA encoded by the gag-pol region of the virus, RNA encoded by the pol gene, env gene, and vif gene, and RNA from the U5 region of the LTR.

DEFINITIONS

Figure 1A:
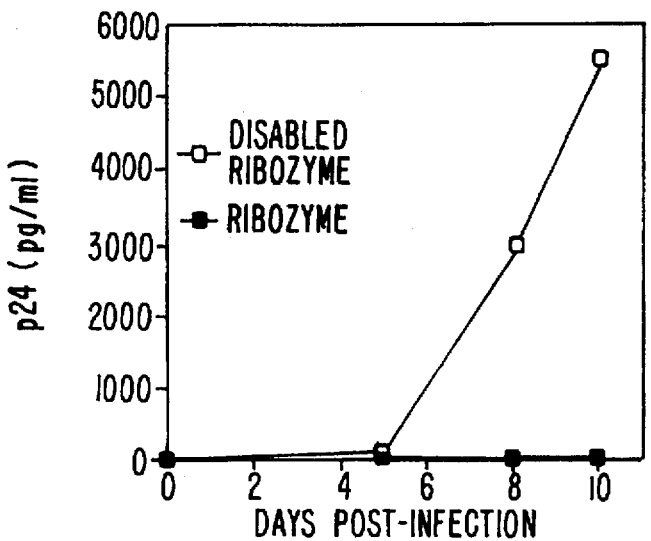
FIG. 1 shows the in vivo inhibitory effect of GUC ribozymes on HIV replication.

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York); Walker (ed) (1988) *The Cambridge Dictionary of Science and Technology*, The press syndicate of the University of Cambridge, NY; and Hale and Marham (1991) *The Harper Collins Dictionary of Biology* Harper Perennial, NY provide one of skill with a general dictionary of many of the terms used in this invention. Paul (1993) *Fundamental Immunology, Third Edition* Raven Press, New York, NY and the references cited therein provide one of skill with a general overview of the ordinary meaning of many of the virally or immunologically related terms herein. Although any methods and materials similar or equivalent to those described herein can be used in the practice or testing of the present invention, preferred methods and materials are described. For purposes of the present invention, the following terms are defined below.

An "endo-ribonuclease nucleic acid" is a nucleic acid which encodes a ribozyme which catalytically cleaves RNA. For example, the endo-ribonuclease nucleic acid is optionally a DNA encoding the ribozyme (either the sense or anti-sense strand). In another embodiment, the endo-ribonuclease nucleic acid is optionally an RNA which can be reverse transcribed into a DNA encoding the ribozyme. In yet another embodiment, the endo-ribonuclease nucleic acid is the ribozyme.

A "ribozyme" is a catalytic RNA molecule which cleaves RNA. The preferred class of ribozymes for the invention is the hairpin ribozyme. In particular, preferred hairpin ribozymes cleave target RNA molecules in trans. A ribozyme cleaves a target RNA in vitro when it cleaves a target RNA in solution. A ribozyme cleaves a target RNA in vivo when the ribozyme cleaves a target RNA in a cell. The cell is optionally isolated, or present with other cells, e.g., as part of a tissue, tissue extract, cell culture, or live organism. For example, a ribozyme is active in vivo when it cleaves a target RNA in a cell present in an organism such as a mammal, or when the ribozyme cleaves a target RNA in a cell present in cells or tissues isolated from a mammal, or when it cleaves a target RNA in a cell in a cell culture.

A "GUA site" is an RNA subsequence found in an RNA molecule which includes the nucleic acids GUA.

A "GUC site" is an RNA subsequence found in an RNA molecule which includes the nucleic acids GUC.

An "HIV encoded nucleic acid" is a nucleic acid which is coded for by the genomic RNA or proviral DNA form of the HIV genome. Such nucleic acids include, inter alia, the full-length RNA genome, unspliced nuclear RNA transcribed from an integrated provirus, and spliced messenger RNA coding for HIV proteins.

A nucleic acid is "operably linked to a promoter" when there is a functional linkage between a nucleic acid expression control sequence (such as a promoter, or array of transcription factor binding sites) and a second nucleic acid sequence (such as a nucleic acid for a heterologous nucleic acid), wherein the expression control sequence directs transcription of the nucleic acid corresponding to the second sequence.

An "expression vector" includes a recombinant expression cassette which has a nucleic acid which encodes an RNA that can be transcribed by a cell. A "recombinant expression cassette" is a nucleic acid construct, generated recombinantly or synthetically, with a series of specified nucleic acid elements which permit transcription of an encoded nucleic acid in a target cell. The expression vector can be part of a plasmid, virus, or nucleic acid fragment. Typically, the recombinant expression cassette portion of an expression vector includes a nucleic acid to be transcribed, and a promoter. In some embodiments, the expression cassette also includes, e.g., an origin of replication, and/or chromosome integration elements such as retroviral LTRs, or adeno associated viral (AAV) ITRs. A "promoter" is an array of nucleic acid control sequences which direct transcription of an associated nucleic acid. As used herein, a promoter includes nucleic acid sequences near the start site of transcription, such as a polymerase binding site. The promoter also optionally includes distal enhancer or repressor elements which can be located as much as several thousand base pairs from the start site of transcription. A "constitutive" promoter is a promoter which is active under most environmental conditions and states of development or cell differentiation, such as a pol III promoter. An "inducible" promoter responds to an extracellular stimulus.

The term "recombinant" when used with reference to a cell indicates that the cell replicates or expresses a nucleic acid, or expresses a peptide or protein encoded by a nucleic acid whose origin is exogenous to the cell. Recombinant cells can express nucleic acids that are not found within the native (non-recombinant) form of the cell. Recombinant cells can also express genes found in the native form of the cell, wherein the genes are re-introduced into the cell by artificial means, for example under the control of a heterologous promoter.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences derived from unrelated genes arranged to make a new functional nucleic acid. For example, in one embodiment, the nucleic acid has a promoter from one gene, such as a human t-RNA gene, arranged to direct the expression of a coding sequence from a different gene, such as an artificial gene coding for a ribozyme. When used with reference to a ribozyme, the term "heterologous" means that the ribozyme is expressed in a cell or location where it is not ordinarily expressed in nature, such as in a T cell which encodes the ribozyme in an expression cassette.

The term "subsequence" in the context of a particular nucleic acid refers to a region of the nucleic acid equal to or smaller than the particular nucleic acid or polypeptide.

A "pol III promoter" is a DNA sequence competent to initiate transcription of associated DNA sequences by pol III. Many such promoters are known, including those which direct expression of known t-RNA genes. Various t-RNA genes are described in Watson et al. *Molecular Biology of The Gene* Fourth Edition, The Benjamin Cummings Publishing Co., Menlo Park, CA pages 710–713.

"helix 1" ribozyme domain is the portion of a nucleic acid encoding the ribozyme which is complementary to a target RNA 3' of the cleavage site on the target RNA, i.e., the ribozyme nucleic acid sequences 5' of the ribozyme nucleic acid subsequence which aligns with the target cleavage site.

A vector "transduces" a cell when it transfers nucleic acid into the cell. A cell is "stably transduced" by a nucleic acid when a nucleic acid transduced into the cell becomes stably replicated by the cell, either by incorporation of the nucleic acid into the cellular genome, or by episomal replication. A vector is "infective" when it transduces a cell, replicates, and (without the benefit of any complementary vector) spreads progeny vector of the same type as the original transducing vector to other cells in an organism or cell culture, wherein the progeny vectors have the same ability to reproduce and spread throughout the organism or cell culture.

DETAILED DESCRIPTION OF THE INVENTION

RNA and DNA molecules encoding ribozymes and ribozyme targets are provided. A ribozyme is a catalytic RNA molecule that cleaves other RNA molecules having nucleic acid sequences that are complementary to particular targeting sequences in the ribozyme. Castanotto et al (1994) *Advances in Pharmacology* 25:289–317 provides and overview of ribozymes in general, including group I ribozymes, hammerhead ribozymes, hairpin ribozymes, RNAse P, and axhead ribozymes. The production of certain ribozymes which specifically target particular HIV sequences are taught in the art (see, e.g., Yu et al. (1993) *Proc. Natl. Acad. Sci. USA* 90:6340–6344) and Dropulic et al. (1992) *Journal of Virology* 66(3):1432–1441; Wong-Staal et al., WO 94/26877). However, the identification of any particular ribozyme target which is cleaved in a cell is unpredictable, because the interaction between the nucleic acid bearing the target sequence, the ribozyme and the cellular environment are not defined. See, e.g., Ojwang et al. (1992) *Proc. Natl. Acad. Sci. USA* 89:10802–10806. This invention identifies significant new HIV targets which are cleaved in vivo, and which inhibit HIV replication in vivo.

The general features of hairpin ribozymes are described e.g., in Hampel et al. (1990) *Nucl. Acids Res.* 18:299–304; Hempel et al., (1990) European Patent Publication No. 0 360 257; U.S. Pat. No. 5,254,678, issued Oct. 19, 1993; Wong-Staal et al., WO 94/26877; Ojwang et al. (1993) *Proc Natl Acad Sci USA* 90:6340–6344; Yamada et al. (1994) *Human Gene Therapy* 1:39–45; Leavitt et al. (1995) *Proc Nail Acad Sci USA* 92:699–703; Leavitt et al. (1994) *Human Gene Therapy* 5:1151–1120; and Yamada et al. (1994) *Virology* 205:121–126. Intracellular expression of certain hairpin ribozymes directed against HIV RNA has been shown to confer significant resistance to HIV infection.

Hairpin ribozymes typically cleave one of two target sequences. GUC ribozymes cleave an RNA target sequence consisting of NNNBCN*GUCNNNNNNNN (SEQ ID NO:1) (where N*G is the cleavage site, B is any of G, U or C, and where N is any of G, U, C, or A). GUA ribozymes typically cleave an RNA target sequence consisting of NNNNN*GUANNNNNNNN. (SEQ ID NO:2) (where N*G is the cleavage site and where N is any of G, U, C, or A). See, De Young et al. (1995) *Biochemistry* 34:15785–15791.

Making Ribozymes and Target Nucleic acids

RNA and DNA nucleic acids, including ribozymes, nucleic acids encoding ribozymes, ribozyme targets, and nucleic acids encoding ribozyme targets, can be synthesized chemically according to known methods such as the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Purification of the molecules, where necessary, is typically performed by either gel electrophoresis or by anion-exchange HPLC as described in Pearson and Regnier (1983) *J. Chrom.* 255:137–149. The sequence of the synthetic DNA and RNA molecules can be verified using the chemical degradation method of Maxam and Gilbert (1980) in Grossman and Moldave (eds.) Academic Press, New York, Methods in Enzymology 65:499–560.

Ribozymes optionally comprise non-standard ribonucleotide bases, or deoxyribonucleotide bases, which can stabilize the ribozyme and make it resistant to RNase enzymes. Alternatively, the ribozyme can be modified to the phosphothio analog for use in liposome delivery systems. This modification also renders the ribozyme resistant to endonuclease activity.

Alternatively, ribozymes are prepared from a DNA molecule comprising an expression cassette that, upon transcription, yields a ribozyme of the invention. An expression cassette of the invention comprises a promoter sequence (e.g., a polymerase II promoter, a polymerase III promoter, or the like) operably linked to a sequence encoding the ribozyme.

Various promoters can be used to direct expression of the ribozymes of the invention, depending on the application. Typically, expression of the construct is high enough to inhibit the growth, infection or replication of the virus (e.g., HIV) against which protection is sought. Accordingly, strong promoters are useful for directing expression of the ribozymes. Such promoters include, but are not limited to, pol III promoters such as the U1, 5S RNA and t-RNA promoters (e.g., the human tRNA$^{val}$ promoter; see, Wong-Staal et al. WO 94/26877); strong constitutive cellular promoters known to persons of skill, including the U1 promoter, the β-actin promoter and the tubulin promoter; viral pol II promoters such as SV 40 promoters and RSV LTR promoters, and tissue specific promoters such as the CD4 promoter.

General cloning methodologies to produce nucleic acids which encode ribozymes or ribozyme targets of the invention are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, CA (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, MO), R&D systems (Minneapolis, MN), Pharmacia LKB Biotechnology (Piscataway, NJ). CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersberg, MD), Fluka Chemica-Biochemika Analytika (Fluka Chemie AG, Buchs, Switzerland), and Applied Biosystems (Foster City, CA), as well as many other commercial sources known to one of skill.

The nucleic acid compositions of this invention, whether RNA, DNA, cDNA, -genomic DNA, genomic RNA or a hybrid of the various combinations, are isolated from natural sources, cloned heterologous sources, or synthesized in vitro. The nucleic acids claimed are present in transduced or transfected whole cells, in transduced or transfected cell lysates, or in a partially purified or substantially pure form.

In vitro amplification techniques are suitable for amplifying RNA or DNA sequences for use as molecular probes, RNA endonucleases (i.e., where the RNA is a ribozyme) or generating nucleic acids for subsequent subcloning. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, CA (1990) (Innis); Amheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lornell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13:563–564. Improved methods of cloning in vitro amplified nucleic acids are described in Wallace et al., U.S. Pat. No. 5,426, 039.

Making Ribozymes Based on Those in the Sequence Listings.

The identification of a target and a ribozyme which cleaves the target effectively in vivo is unpredictable. However, once a target RNA is identified (e.g., by virtue of a GUC or GUA), and a ribozyme is constructed which cleaves the target in vivo, one of skill can generate many similar targets and ribozymes by performing routine modification of the given targets and ribozymes. For instance, lengthening or shortening the helix 1 or helix 2 domain of the ribozyme can have an effect on the activity of the ribozyme. See, Anderson et al. (1994) *Nucleic Acids Research* 22(6):1096–1100. Thus, for each of the ribozymes in the sequence listings herein, one of skill will readily recognize that many ribozymes consist essentially of the given sequence, differing only by the number of nucleotides complementary to the target RNA in the helix 1 or helix 2 domains of the ribozyme. Preferred ribozymes have a helix one length of from about 4 to about 20 bases complementary to a nucleotides flanking the cleavage site. For example, in one class of embodiments, helix 1 has about 6 to about 12 complementary nucleotides. For instance, in certain ribozymes described in the Examples below, the helix one domain is about 8 nucleotides in length.

Similarly, one of skill will understand that the target sequences given in the sequence listings can be depicted as the given sequence, or as the given sequence plus additional flanking sequence, or with some of the nucleotides flanking the cleavage site deleted. Such different depictions do not change the essential nature of the target site, and it is understood that alternately represented target sites consist essentially of the given targets. In addition, the target can be modified by the substitution of one or a few nucleotides in the target. For example, viral variants which encode changes in helix 1 and/or helix 2 binding sites can be cleaved by ribozymes which have compensatory changes in helix 1 or helix 2.

In addition to the simple modification of helix 1 or helix 2, other simple modifications are also possible which effect the activity of the ribozyme. For instance, the helix 3 and helix 4 regions can be lengthened or shortened by the addition or subtraction of nucleotides in these helices (see, e.g., FIG. 3). The position of individual complementary nucleotides in the helices can be reversed. The loop 3 domain can be substituted with a variety of nucleotides. See, e.g., the figures and examples herein.

Thus, the ribozymes in the sequence listing are optionally modified by making loop 3 nucleotide substitutions, helix 4 nucleotide substitutions, lengthening or shortening the helix 4 domain, lengthening or shortening the helix 3 domain, or lengthening or shortening the helix 1 or helix 2 domain. Furthermore, as described above, the ribozymes of the sequence listing can be modified by incorporation of non-standard ribonucleotides or deoxyribonucleotides and/or conversion of the ribozyme to an RNA phosphothio analog. One of skill will readily appreciate that such minor modification of the given ribozymes is possible, and that the methods of making and screening the modifications is straightforward, and is performed by adapting the ribozymes described herein. Accordingly, it will immediately be recognized that each ribozyme in the sequence listings can be modified in a variety of ways to yield similar ribozymes with similar or identical activity.

In one preferred embodiment, stabilizing elements are incorporated into the expressed ribozyme to increase the stability of the ribozyme. For instance, the HIV rev response element (RRE) which stabilizes HIV transcripts (or a minimal Rev binding sequence thereof) is incorporated into the ribozyme to stabilize the ribozyme, and to direct the ribozyme to the same cellular location as HIV message RNA (Yamada 1995, supra). See, Wong-Staal et al. (1991) "Viral And Cellular Factors that Bind to the Rev Response Element" in *Genetic Structure and Regulation of HIV* (Haseltine and Wong-Staal eds.; part of the Harvard AIDS Institute Series on Gene Regulation of Human Retroviruses, Volume 1), pages 311–322 and the references cited therein. Another example of an RNA stabilizing element is the 340 bp insert from the Mason Pfizer Monkey Virus (MPMV) which is sufficient to target nucleic acids to the cytosol. See, Bray et al. (1994) *Proc. Natl. Acad. Sci. USA* 91:1256–1260. In other embodiments, the target binding sequence is altered to match homologous sites on other HIV strains. The identification of a target cleaved by a ribozyme in vitro and in vivo, and the sequence of a ribozyme which cleaves the target provides one of skill with information sufficient for constructing structurally similar ribozymes that cleave the identified target.

In Vitro Uses For the Ribozymes of the Invention

The ribozymes of the invention are generally useful for their endo-ribonuclease activity. The ability to specifically cleave RNAs in vitro is used to prepare RNAs for cloning, e.g. , prior to reverse transcription into cDNA and cloning. For example, an RNA which comprises a target subsequence can be cleaved by an appropriate ribozyme to yield two RNAs. The RNAs can then be cloned for further analysis. Thus, ribozymes provide a commercially valuable scientific tool useful in recombinant construction of nucleic acids. Tools which perform similar functions, such as DNA endonucleases (restriction enzymes), are widely used and highly valuable.

The ability to cleave target RNA in vitro also provides an assay for the presence or availability of the RNA target site. For instance, HIV RNA comprising a target can be detected by cleaving the RNA with a ribozyme and detecting the resulting fragments with an appropriate probe or probes. Sambrook describes methods of detecting RNAs, such as northern blotting.

In addition to chemical synthesis of the ribozymes, the ribozymes are also made by cloning DNA encoding the ribozymes into known expression systems in vitro, and in bacteria, yeast, mammalian cells, plants and the like, and purifying the ribozymes using standard techniques for RNA isolation. Sambrook, Ausbel and Berger provide an introduction to gene expression systems.

Ribozymes are typically active in vitro, e.g., in tris-based buffers containing $Mg^{++}$ and optionally other salts. Spermidine is also added to many in vitro buffers. For instance, one typical in vitro buffer for assaying ribozyme activity is 40 mM Tris-HCl pH 7.5, 10 mM $MgCl_2$ and 2 mM spermidine.

In Vivo Uses for the Ribozymes of the Invention; Preferred Cell Transduction Vectors In preferred embodiments, the cellular expression of the ribozymes of the invention inhibits infection and replication of HIV in cells. This property is useful in cell and tissue culture, where inadvertent infection of cells by HIV is dangerous to people handling the cells. In more preferred embodiments, the ability of the ribozymes of the invention to inhibit HIV infection is used to inhibit or ameliorate HIV infection in a patient.

Vectors exist for the delivery of transcription cassettes comprising the ribozymes of the invention in organismal in vivo procedures and in ex vivo procedures. Examples of vectors include those described in Wong-Staal et al., WO 94/26877; Sullenger et al. (1990) *Molecular and Cellular Biology* 10(12):6512–6523; Gilboa et al. (PCT publication WO 90/13641, and Chatterjee et al. (1992) Science 258:1485–1487.

Organismal cellular transduction provides methods for combating chronic infectious diseases such as AIDS, caused by HIV infection, as well as non-infectious diseases such as cancer. Yu et al. (1994) *Gene Therapy* 1:13–26 and the references therein provides a general guide to gene therapy strategies for HIV infection. See also, Sodoski et al. PCT/US91/04335. Wong-Staal et al., WO/94/26877 describe retroviral gene therapy vectors.

Common organismal cellular transduction vectors include, but are not limited to, those derived from murine retroviruses (including MoMLv), avian rous sarcoma virus (RSV), Hepatocyte viruses, HIV-1, HIV-2, and adeno-associated virus (AAV)-based vectors.

The majority of the approved gene transfer trials in the United States rely on replication-defective murine retroviral vectors harboring a therapeutic polynucleotide sequence as part of the retroviral genome (Miller et al. *Mol. Cell. Biol.* 10:4239 (1990); Kolberg R J. NIH Res. 4:43 (1992); Cornetta et al. *Hum. Gene Ther.* 2:215 (1991)). Murine retroviral vectors have been used to stably introduce ribozyme genes into target cells, and similar approaches can be used for the ribozymes of the invention. See, Yamada et al. (1994) *Gene Therapy* 1:38–45.

AAVs utilize helper viruses such as adenovirus or herpes virus to achieve productive infection. In the absence of helper virus functions, wild-type AAV integrates (site-specifically) into a host cell's genome, but the integrated AAV genome has no known pathogenic effect. The integration step allows the AAV genome to remain genetically intact until the host is exposed to the appropriate environmental conditions (e.g., a lyric helper virus), whereupon it re-enters the lyric life-cycle. Samulski (1993) *Current Opinion in Genetic and Development* 3:74–80 and the references cited therein provides an overview of the AAV life cycle. For a general review of AAVs and of the adenovirus or herpes helper functions see, Berns and Bohensky (1987) *Advanced in Virus Research, Academic Press.*, 32:243–306. The genome of AAV is described in Laughlin et al. (1983) *Gene,* 23:65–73. Expression of AAV is described in Beaton et al. (1989) *J. Viro* 63:4450–4454.

AAV-based vectors are used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4:2072–2081; Hermonat and Muzyczka (1984) *Proc. Natl. Acad. Sci. USA*, 81:6466–6470; McLaughlin et al. (1988) and Samulski et al. (1989) *J. Virol.,* 63:03822–3828. Cell lines that can be transduced by rAAV include those described in Lebkowski et al. (1988) *Mol. Cell. Biol.,* 8:3988–3996.

Recombinant AAV vectors (rAAV vectors) deliver foreign nucleic acids to a wide range of mammalian cells (Hermonat & Muzycka (1984) *Proc Natl Acad Sci USA* 81:6466–6470; Tratschin et al. (1985) *Mol Cell Biol* 5:3251–3260), integrate into the host chromosome (Mclaughlin et al. (1988) *J Virol* 62:1963–1973), and show stable expression of the transgene in cell and animal models (Flotte et al. (1993) *Proc Natl Acad Sci USA* 90:10613–10617). rAAV vectors are able to infect non-dividing cells (Podsakoff et al. (1994) *J Virol* 68:5656–66; Flotte et al. (1994) *Am. J. Respir. Cell Mol. Biol.* 11:517–521). Further advantages of rAAV vectors include the lack of an intrinsic strong promoter, thus avoiding possible activation of downstream cellular sequences, and the vector's naked icosohedral capsid structure, which renders the vectors stable and easy to concentrate by common laboratory techniques.

rAAV vectors are used to inhibit, e.g., viral infection, by including anti-viral transcription cassettes in the rAAV vector. For example, Chatterjee et al. (*Science* (1992), 258:1485–1488) describe anti-sense inhibition of HIV-1 infectivity in target cells using an rAAV vector with a constitutive expression cassette expressing anti-TAR RNA. Chatterjee et al. (PCT application PCT/US91/03440 (1991), hereinafter Chatterjee et al. 2) describe rAAV vectors, including rAAV vectors which express antisense TAR sequences. Chatterjee and Wong (*Methods, A companion to Methods in Enzymology* (1993), 5:51–59) further describe rAAV vectors for the delivery of antisense RNA. These known vectors can be modified by substituting the anti-sense sequences in the vectors with the ribozymes of the invention.

HIV based vectors and AAV based vectors are used for transduction of $CD4^+$ cells, because they do not require actively dividing cells for transduction (unlike murine retroviruses). In some applications, HIV vectors are used, because they typically only infect $CD4^+$ cells in an organism, i.e., those cells which are infected by HIV viruses.

When using retroviral vectors, packaging cells are commonly used to prepare the virions used to transduce the target cells. In these cells, trans active genes rendered inactive in a gene therapy vector are "rescued" by trans complementation to provide a packaged vector. For instance, cells transduced with HIV or murine retroviral proviral sequences which lack the nucleic acid packaging site produce retroviral trans active components, but do not specifically incorporate the retroviral nucleic acids into the capsids produced, and therefore produce little or no live virus. When these transduced "packaging" cells are subsequently transduced or transfected with a vector nucleic acid which lacks coding sequences for retroviral trans active functions, but includes sequences necessary for packaging, reverse transcription and integration, the vector nucleic acid is packaged into an infective virion. A number of packaging cell lines useful for MoMLV-based vectors are known in the art, such as PA317 (ATCC CRL 9078) which expresses MoMLV core and envelope proteins see, Miller et al. (1991) *J. Virol.* 65:2220–2224. Carrol et al. (1994) *Journal of virology* 68(9):6047–6051 describe the construction of packaging cell lines for HIV viruses.

Functions of viral replication not supplied by trans-complementation which are necessary for transduction of the vector are present in the vector. For HIV based vectors, this typically includes, e.g., the TAR sequence, the sequences necessary for HIV packaging, the RRE sequence if the instability elements of the p17 gene of gag is included, and sequences encoding the polypurine tract. HIV sequences that contain these functions include a portion of the 5' long terminal repeat (LTR) and sequences downstream of the 5' LTR responsible for efficient packaging, i.e., through the major splice donor site ("MSD"), and the polypurine tract upstream of the 3' LTR through the U3R section of the 3' LTR. The packaging site (psi site or ψ site) is located adjacent to the 5' LTR, primarily between the MSD site and the gag initiator codon (AUG) in the leader sequence. See, Garzino-Demo et al. (1995) *Hum. Gene Ther.* 6(2):177–184. For a general description of the structural elements of the HIV genome, see, Holmes et al. PCT/EP92/02787.

The present invention provides several features that allow one of skill to generate powerful gene therapy vectors (including, but not limited to AAV vectors, HIV vectors and RSV vectors) against specific cellular targets, in vitro and in vivo, e.g., against CD4$^+$ cells. For example, CD4$^+$ cells are infected by HIV viruses, and transduced by HIV-based vectors. Lists of CD4$^+$ and CD4$^-$ cell types which are infectable by HIV have been compiled (see, Rosenburg and Fauci 1 supra; Rosenburg and Fauci (1989) *Adv Immunol* 47:377–431; and Connor and Ho (1992) in *AIDS: etiology, diagnosis, treatment, and prevention*, third edition Hellman and Rosenburg (eds) Lippincott, Philadelphia).

In addition to CD4$^+$ cells, transduction of CD34$^+$ hematopoietic stem cells by vectors encoding the ribozymes of the invention is also highly desirable. These stem cells differentiate into a variety of immune cells, including CD4$^+$ cells which are the primary targets for HIV infection. CD34$^+$ cells are the most important target cells for ex vivo gene therapy, because these cells differentiate into many different cell types, and because the cells are capable of re-engraftment into a patient undergoing ex vivo therapy.

HIV-based vectors are made competent to transduce CD34$^+$ cells by pseudotyping the vector. This is done by transducing the packaging cell line used to package the vector with a nucleic acid which encodes the vesicular stomatitis virus (VSV) envelope protein, which is then expressed on the surface of the HIV vector. VSV infects CD34$^+$ cells, and pseudotype vectors expressing VSV envelope proteins are competent to transduce these cells.

Nucleic acids encoding ribozymes of the invention are useful as components of gene therapy vectors. Retroviral vectors packaged into HIV envelopes primarily infect CD4$^+$ cells, (i.e., by interaction between the HIV envelope glycoprotein and the CD4 "receptor") including, non-dividing CD4$^+$ cells such as macrophage. For instance, nucleic acids which encode ribozymes are encapsidated into HIV capsids in gene therapy vectors which include an HIV packaging site (e.g., the $\psi$ site in HIV, see, Aldovini and Young (1990) *Journal of Virology* 64(5):1920–1926, and Clever et al. (1995) *Journal of Virology* 69(4):2101–2109), and typically also include the HIV LTR 'sequences. Thus, in one embodiment, the ribozymes of the present invention are incorporated into HIV-based gene therapy vectors which deliver the ribozymes to CD4$^+$ or CD34$^+$ cells. This is accomplished by incorporating cis active nucleic acids (e.g., promoter sequences, packaging sequences, integration or cellular targeting sequences) into the vector, or by using trans active nucleic acids and polypeptides (capsid and envelope proteins and transcription factors) to replicate and package the gene therapy vector into an viral capsid (e.g., an HIV capsid and envelope), or both. See, e.g., Poznansky et al. (1991) *Journal or Virology* 65(1):532–536 and Garzino Demo et al. (supra) for a description of the of the region flanking the 5' HIV LTR.

Ex Vivo Transduction of Cells

Ex vivo methods for inhibiting viral replication in a cell in an organism involve transducing the cell ex vivo with a therapeutic nucleic acid of this invention, and introducing the cell into the organism. The cells are typically CD4$^+$ cells such as CD4$^+$ T cells or macrophage isolated or cultured from a patient, or are stem cells. Alternatively, the cells can be those stored in a cell bank (e.g., a blood bank).

The ribozymes of the invention inhibit viral replication in cells already infected with HIV virus, in addition to conferring a protective effect to cells which are not infected by HIV. In addition, in one class of embodiments, the vector is replicated and packaged into HIV capsids using the HIV replication machinery, thereby causing the anti-HIV ribozyme to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides compositions and methods for protecting cells in culture, ex vivo and in a patient, even when the cells are already infected with the virus against which protection is sought.

The culture of cells used in conjunction with the present invention, including cell lines and cultured cells from tissue or blood samples is well known in the art. Freshney (*Culture of Animal Cells, a Manual of Basic Technique*, third edition Wiley-Liss, New York (1994)) and the references cited therein provides a general guide to the culture of cells. Transduced cells are cultured by means well known in the art. See, also Kuchler et al. (1977) *Biochemical Methods in Cell Culture and Virology*, Kuchler, R. J., Dowden, Hutchinson and Ross, Inc. Mammalian cell systems often will be in the form of monolayers of cells, although mammalian cell suspensions are also used. Illustrative examples of mammalian cell lines include VERO and Hela cells, Chinese hamster ovary (CHO) cell lines, W138, BHK, Cos-7 or MDCK cell lines (see, e.g., Freshney, supra).

In one embodiment, CD34$^+$ stem cells (which are typically not CD4$^+$) are used in ex-vivo procedures for cell transduction and gene therapy. The advantage to using stem cells is that they can be introduced into a mammal (such as the donor of the cells) where they will engraft in the bone marrow.

In humans, CD34 cells can be obtained from a variety of sources including cord blood, bone marrow, and mobilized peripheral blood. Purification of CD34$^+$ cells can be accomplished by antibody affinity procedures. Wong-Staal et al. WO 94/26877 describe methods of isolating and transforming CD34$^+$ cells. An affinity column isolation procedure for isolating CD34$^+$ cells is described by Ho et al. (1995) *Stem Cells* 13 (suppl. 3):100–105. See also, Brenner (1993) Journal of Hematotherapy 2:7–17. Yu et al. (1995) *PNAS* 92:699–703 describe a method of transducing CD34$^+$ cells from human fetal cord blood using retroviral vectors.

Rather than using stem cells, T cells are also used in some embodiments in ex vivo procedures. Several techniques are known for isolating T cells. One procedure for isolating T cells is described in Leavitt et al. *Hum. Gene Ther.* (1994) 5:1115–1120. Wong-Staal et al. WO 94/26877 also describes methods of isolating and transforming T cells. HIV inhibitors are typically added to cultures of T-cells to inhibit HIV growth when the T cells are isolated from potentially HIV-positive sources. For example, delaviridine can be added to cultures of T cells at a concentration of from about 1 to about 10 µM to inhibit HIV growth.

The expression of surface markers facilitates identification and purification of T cells. Methods of identification and isolation of T cells include FACS, incubation in flasks with fixed antibodies which bind the particular cell type and panning with magnetic beads.

Administration of Vectors and Transduced Cells

Vectors comprising endo-ribonuclease nucleic acids can be administered directly to a patient for transduction of cells in the patient. Administration is by any of the routes normally used for introducing a molecule into ultimate contact with blood or tissue cells. Vector packaged nucleic acids encoding the ribozymes of the invention are administered in any suitable manner, preferably with pharmaceutically acceptable carriers. Alternatively, the nucleic acids can be naked, or present in a liposome. Suitable methods of administering such nucleic acids in the context of the present invention to a patient are available.

Pharmaceutically acceptable carriers are determined in part by the particular composition being administered, as well as by the particular method used to administer the composition. Accordingly, there is a wide variety of suitable formulations of pharmaceutical compositions of the present invention. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are suitable methods of administration. The formulations of packaged nucleic acid can be presented in unit-dose or multi-dose sealed containers, such as ampules and vials.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of virally-mediated diseases such as AIDS, the physician evaluates circulating plasma levels, vector and ribozyme toxicities, progression of the disease, and the production of anti-vector antibodies.

For administration, ribozymes and transducer cells of the present invention can be administered at a rate determined by the LD-50 of the ribozyme, vector, or ribozyme-transduced cell type, and the side-effects of the ribozyme, vector or cell type at various concentrations, as applied to the mass and overall health of the patient. Administration can be accomplished via single or divided doses.

Transduced cells are prepared for reinfusion according to established methods. See, Abrahamsen et al. (1991) *J. Clin. Apheresis* 6:48–53; Carter et al. (1988) *J. Clin. Apheresis* 4:113–117; Aebersold et al. (1988), *J. Immunol. Methods* 112:1–7; Muul et al. (1987) *J. Immunol. Methods* 101:171–181 and Carter et al. (1987) *Transfusion* 27:362–365. In one class of ex vivo procedures, between $1\times10^4$ and $1\times10^{12}$ transducer cells (e.g., stem cells or T cells transduced with vectors encoding the ribozymes of the invention) are infused intravenously, e.g., over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion may be repeated about every 2 to 3 months for a total of 4 to 6 treatments in a one year period. After the first treatment, infusions can be performed on a outpatient basis at the discretion of the clinician.

If a patient undergoing infusion of a vector or transduced cell develops fevers, chills, or muscle aches, he/she typically receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

The effect of the therapeutic vectors or transduced cells of the invention on HIV infection and AIDS are measured by monitoring the level of HIV virus in a patient, or by monitoring the $CD4^+$ cell count for the patient over time. Typically, measurements are taken before, during and after the therapeutic regimen. Kits for detecting and quantitating HIV, and $CD4^+$ cells are widely available. Virus and $CD4^+$ cells can be detected and quantified using an immunoassay such as an ELISA, or by performing quantitative PCR. Cell sorting techniques such as FACS are often used to isolate and quantify $CD4^+$ cells.

EXAMPLES

The following examples are provided by way of illustration only and not by way of limitation. Those of skill will readily recognize a variety of noncritical parameters which could be changed or modified to yield essentially similar results.

Example 1: Three Novel GUC Ribozymes with Potent in vivo Anti-HIV Activity

This example describes three new GUC hairpin ribozymes with potent anti-HIV activity in vivo. The sequence of the sense strand of the DNA encoding the ribozymes is given in Table 1 (the actual ribozyme sequence is the same as the given sequence, except that ribonucleotides are used and U is substituted for T).

TABLE 1

Sequences of GUC ribozyme genes.

pol 3308 (SEQ ID NO:3)
ATGTCATTAGAAGTCCACCAGAGAAACACACGTTGTGGTATATTACCTGGTA
vif 5251 (SEQ ID NO:4)
TGTATGCAAGAACCAAACCAGAGAAACACACGTTGTGGTATATTACCTGGTA
env 7931 (SEQ ID NO:5)
ATGCCCCAAGAAGTGAACCAGAGAAACACACGTTGTGGTATATTACCTGGTA The three ribozymes were designed to specifically target three conserved regions if HIV, as shown in Table 2.

TABLE 2

| Novel anti-HIV ribozymes and their cleavage sites | | |
|---|---|---|
| Ribozyme | Target Site | Target Sequence |
| pol-2 | 3308 | GGACU*GUCAAUGACAU (SEQ ID NO:6) |
| vif | 5251 | UUGGG*GUCUGCAUACA (SEQ ID NO:7) |
| env-2 | 7931 | UCACA*GUCUGGGGCAU (SEQ ID NO:8) |

Target Site number indicates the site of cleavage as bases from the 5' end of the LTR in $HIV_{HXB2}$.
*is the site of cleavage.

DNA encoding the ribozymes, along with corresponding disabled ribozymes, was synthesized using an automated DNA synthesizer. The strategy for making disabled ribozymes is described, e.g., in Ojwang et al. (1992) *Proc. Natl. Acad. Sci. USA* 89:10802. The DNAs were cloned into described ribozyme transfer vectors pMJT (ATCC#75470; see, Wong-Staal et al., WO 94/26877) and pMFT. pMFT is a derivative of pMJT with an insert (aattcaggactagtcttttaggtcaaaaagaa) in the HindIII site immediately upstream of the t-RNA gene. The native ribozyme gene was altered in the synthesized DNAs so that helix 1 and helix 2 sequences base pair with the particular regions in HIV RNA described in Table 2 (See also, Ojwang et al. (1992) *Proc. Natl. Acad. Sci. USA* 89:10802). Stable Molt 4/8 T cell lines which express ribozymes, disabled ribozymes, or no ribozymes (LNL-6; see, Gertbank accession No. M63653) were produced by transduction and G418 selection. The cultures were then challenged with HIV at a multiplicity of infection (MOI) of 0.01. Virus production was monitored by p24 ELISA using a kit from Coulter Co., Miami, FL.

Figure 1B:
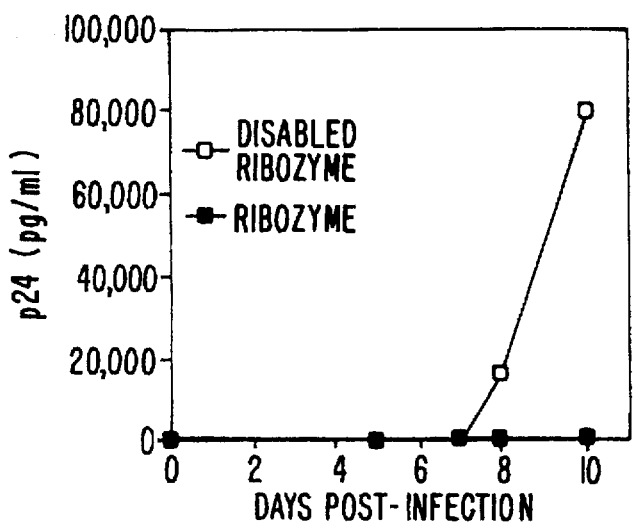
Figure 1C:
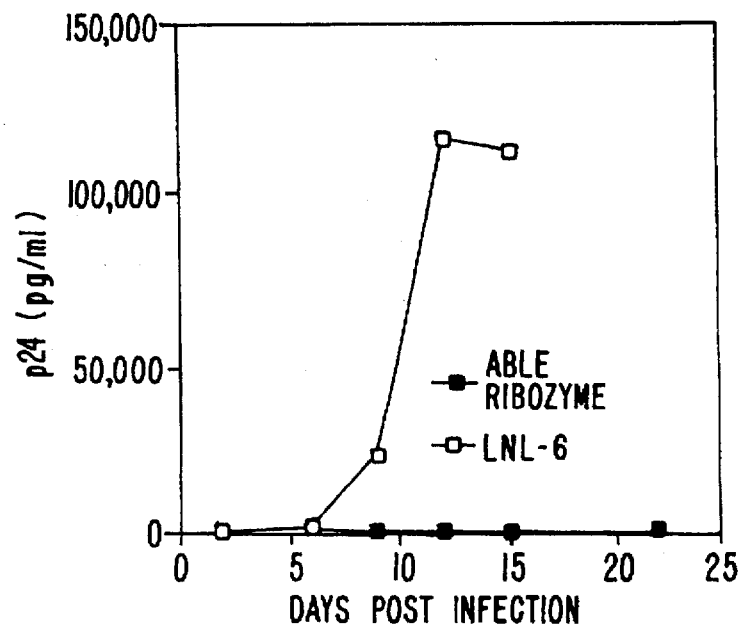

The results are shown in FIG. 1. All three ribozymes completely inhibited HIV replication as measured by p24 production, as compared with controls. The control disabled ribozymes and LNL-6 had no detectable anti-HIV activity.

Figure 2:
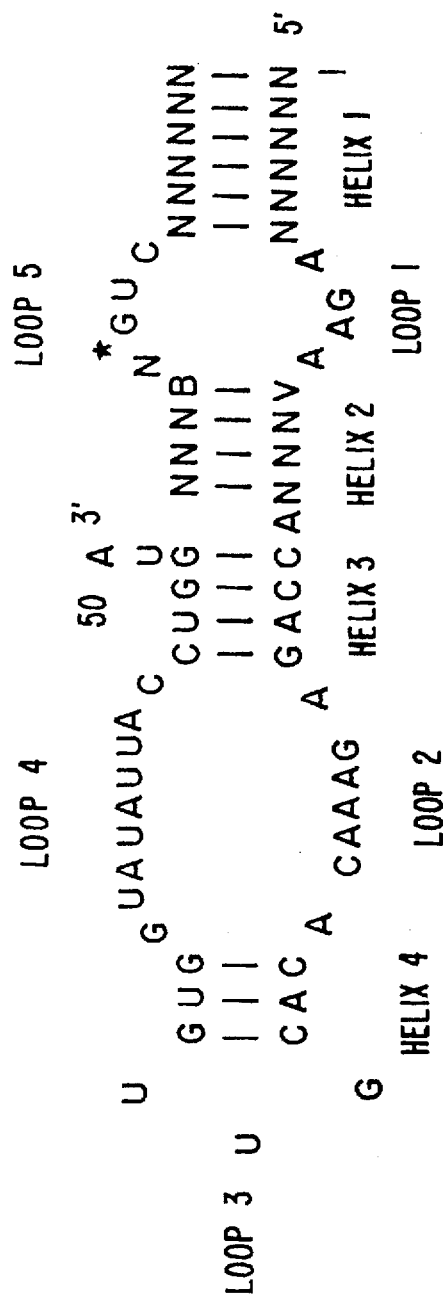
FIG. 2 shows a ribozyme bound to a target RNA with the structural domains of the ribozyme indicated.
Figure 3:
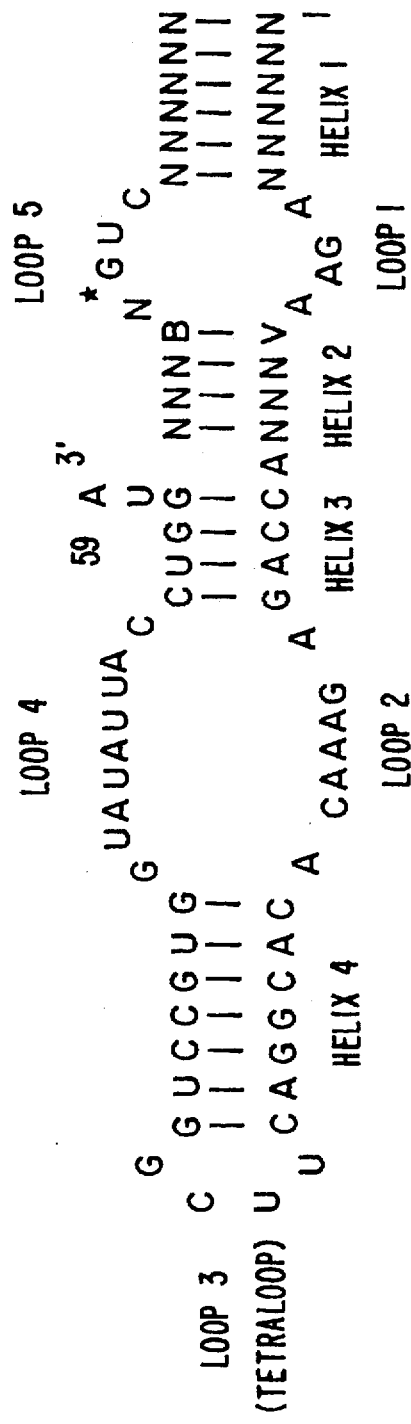
FIG. 3 shows optional loop 3 and helix 4 modifications of the prototype ribozyme.
Figure 4:
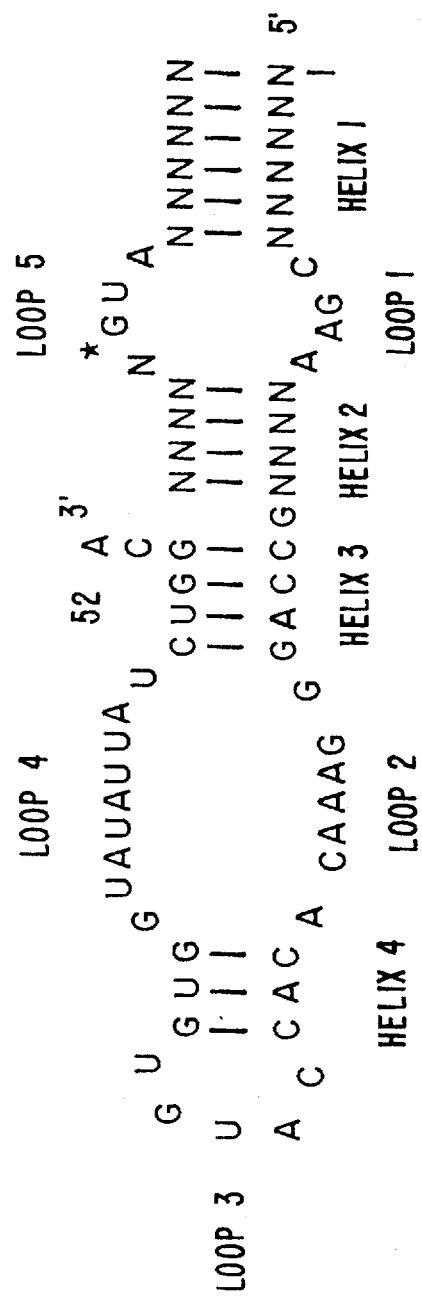
FIG. 4 shows negative strand satellite RNA of Chicory Mosaic Virus-based ribozyme bound to a target RNA.
Figure 5:
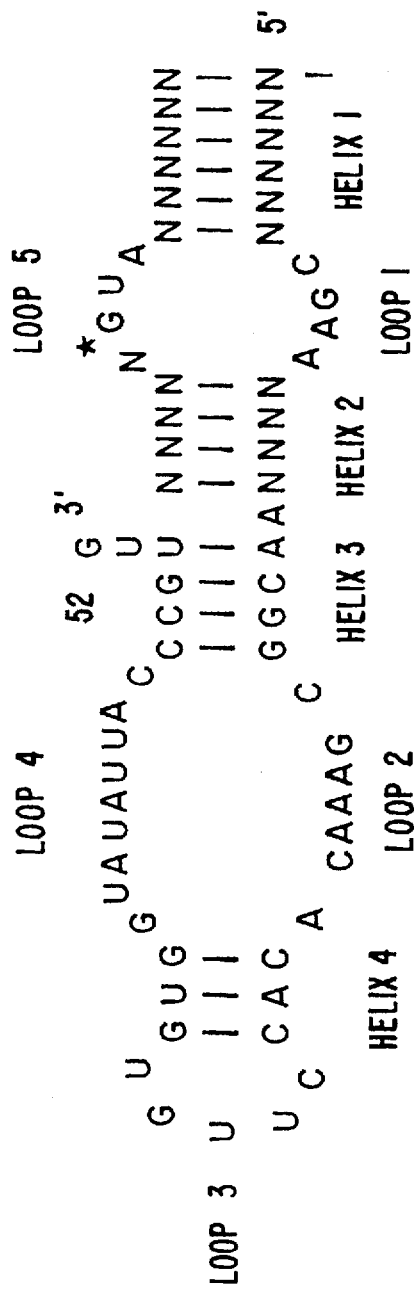
FIG. 5 shows negative strand satellite RNA of an Arabis Mosaic Virus-based ribozyme bound to a target RNA.

One of skill will appreciate that many modifications of the given ribozymes are possible. For instance, the hairpin ribozymes which were used have an arbitrary helix 1 length of 8 bases. The length of helix 1 (see, e.g., FIG. 2) is optionally lengthened or shortened while retaining the basic activity of the ribozyme. In another class of embodiments, the configuration of loop 3 and helix 4 is modified.

In yet another class of embodiments, stabilizing elements are incorporated into the expressed ribozyme to increase the stability of the ribozyme. For instance, the HIV rev response element (RRE) which stabilizes HIV transcripts (or a minimal Rev binding sequence thereof) is incorporated into the ribozyme to stabilize the ribozyme, and to direct the ribozyme to the same cellular location as HIV message RNA. See, Wong-Staal et al. (1991) "Viral And Cellular Factors that Bind to the Rev Response Element" in *Genetic Structure and Regulation of HIV* (Haseltine and Wong-Staal eds.; part of the Harvard AIDS Institute Series on Gene Regulation of Human Retroviruses, Volume 1), pages 311–322 and the references cited therein. Another example of an RNA stabilizing element is the 340 bp insert from the Mason Pfizer Monkey Virus (MPMV) which can target nucleic acids to the cytosol. See, Bray et al. (1994) *Proc. Natl. Acad. Sci. USA* 91:1256–1260. In other embodiments, the target binding sequence is altered to match homologous sites on other HIV strains.

Example 2: Sequences of fourteen GUA ribozymes Which Cleave HIV Targets

This example provides fourteen new GUA ribozymes which cleave GUA targets in HIV. DNA encoding the targets is synthesized on a commercially available automatic DNA synthesizer, and the sequences are cloned into a ribozyme expression vector such as pMJT (see, Example 1). The vector is used to transduce a target cell such as a CD4$^+$ cell, where it cleaves HIV messages in the cell.

Examples of the ribozymes are provided below:

---

A. Examples of the GUA ribozyme genes based on the negative strand satellite RNA of the Arabis Mosaic Virus. The following ribozymes are modified from the negative strand of the Arabis Mosaic Virus (AMV). See, De Young et al. (1995) Biochemistry 34:15785–15791. The sequences below are the sense strand of the DNA which encodes the respective ribozymes.

--- anti-2345 (SEQ ID NO:9)
TCTTCTAACGAAGTATAACGGCGAAACACACCTTGTGTGGTATATTACCCGTTG
anti-2425 (SEQ ID NO:10)
TCTGATCACGAAGTCTAACGGCGAAACACACCTTGTGTGGTATATTACCCGTTG
anti-2480 (SEQ ID NO:11)
GTAGGTCCCGAAAATAAACGGCGAAACACACCTTGTGTGGTATATTACCCGTTG
anti-4154 (SEQ ID NO:12)
TGTGCTGGCGAACATGAACGGCGAAACACACCTTGTGTGGTATATTACCCGTTG
anti-5331 (SEQ ID NO:13)
TCAGGGTCCGAATGTGAACGGCGAAACACACCTTGTGTGGTATATTACCCGTTG
anti-6581 (SEQ ID NO:14)
GTTAATTTCGAACATGAACGGCGAAACACACCTTGTGTGGTATATTACCCGTTG
anti-6963 (SEQ ID NO:15)
TCCATGTGCGAATTGTAACGGCGAAACACACCTTGTGTGGTATATTACCCGTTG B. The Following examples of GUA ribozyme genes are based on the negative strand satellite RNA of Chicory Mosaic Virus. See, De Young et al. (1995) Biochemistry 34: 15785–15791. The sequences below are the sense strand of the DNA which encodes the respective ribozymes.

--- anti-2345 (SEQ ID NO:16)
TCTTCTAACGAAGTATGCCAGGGAAACACACCATGTGTGGTATATTATCTGGCA
anti-2425 (SEQ ID NO:17)
TCTGATCACGAAGTCTGCCAGGGAAACACACCATGTGTGGTATATTATCTGGCA
anti-2480 (SEQ ID NO:18)
GTAGGTCCCGAAAATAGCCAGGGAAACACACCATGTGTGGTATATTATCTGGCA
anti-4154 (SEQ ID NO:19)
TGTGCTGGCGAACATGGCCAGGGAAACACACCATGTGTGGTATATTATCTGGCA
anti-5331 (SEQ ID NO:20)
TCAGGGTCCGAATGTGGCCAGGGAAACACACCATGTGTGGTATATTATCTGGCA
anti-6581 (SEQ ID NO:21)
GTTAATTTCGAACATGGCCAGGGAAACACACCATGTGTGGTATATTATCTGGCA
anti-6963 (SEQ ID NO:22)
TCCATGTGCGAATTGTGCCAGGGAAACACACCATGTGTGGTATATTATCTGGCA The HIV target sites for the above ribozymes (numbering bases from the 5' end of the LTR in HIV$_{HXB2}$) are as follows:
Nucleotide 2345-5' AUACAGUAUUAGAAGA 3' Gag-Pol region (SEQ ID NO:23)

-continued

Nucleotide 2425-5' AGACAGUAUGAUCAGA 3' Pol gene (SEQ ID NO:24)
Nucleotide 2481-5' UAUUAGUAGGACCUAC 3' Pol gene (SEQ ID NO:25)
Nucleotide 4154-5' CAUGGGUACCAGCACA 3' Pol gene (SEQ ID NO:26)
Nucleotide 5331-5' CACAAGUAGACCCUGA 3' Sor 23 K protein (SEQ ID NO:27)
Nucleotide 6581-5' CAUGUGUAAAAUUAAC 3' Env gene (SEQ ID NO:28)
nucleotide 6963-5' ACAAUGUACACAUGGA 3' Env gene (SEQ ID NO:29)

As set forth above for the GUC ribozymes, one of skill will appreciate that many modifications of the given GUA ribozymes are possible. Modifications which would be apparent to one of skill include those described in Example 1 for the GUC ribozymes.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A endo-ribonuclease nucleic acid encoding a ribozyme which cleaves an RNA comprising a target subsequence selected from the group of target subsequences consisting essentially of SEQ ID NO:6, SEQ ID NO:7, SEQ ID NO:8, SEQ ID NO:23, SEQ ID NO:24, SEQ ID NO:25, SEQ ID NO:26, SEQ ID NO:27, SEQ ID NO:28, and SEQ ID NO:29, wherein the endo-ribonuclease nucleic acid comprises a nucleic acid subsequence complementary to the selected target subsequence.

2. The endo-ribonuclease nucleic acid of claim 1, wherein the endo-ribonuclease nucleic acid is selected from the group of endo-ribonuclease nucleic acids consisting of SEQ ID NO:3, SEQ ID NO:4, SEQ ID NO:5, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID No. 22.

3. The endo-ribonuclease nucleic acid of claim 1, wherein the ribozyme cleaves a target nucleic acid 5' of a GUA site.

4. The endo-ribonuclease nucleic acid of claim 1, wherein the ribozyme cleaves a target nucleic acid 5' of a GUC site.

5. The endo-ribonuclease of claim 1, wherein the ribozyme encoded by the nucleic acid cleaves an HIV encoded nucleic acid in a cell, which cell is in isolated form.

6. The endo-ribonuclease nucleic acid of claim 5, wherein the nucleic acid comprises an HIV RRE sequence.

7. The endo-ribonuclease nucleic acid of claim 1, wherein the nucleic acid is operably linked to a promoter.

8. The endo-ribonuclease nucleic acid of claim 7, wherein the promoter is a pol III promoter.

9. The endo-ribonuclease nucleic acid of claim 1, wherein the ribozyme encoded by the nucleic acid cleaves an HIV encoded nucleic acid in vitro.

10. The endo-ribonuclease nucleic acid of claim 1, wherein the endo-ribonuclease nucleic acid encodes a modified ribozyme derived from a ribozyme selected from the group of ribozymes consisting of SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, and SEQ ID No. 20.

11. The endo-ribonuclease nucleic acid of claim 10, wherein the modified ribozyme is derived from the group of ribozymes by increasing the number of complementary nucleotides in helix 1.

12. The endo-ribonuclease nucleic acid of claim 10, wherein the modified ribozyme is derived from the group of ribozymes by decreasing the number of complementary nucleotides in helix 1.

13. The endo-ribonuclease nucleic acid of claim 1, wherein the nucleic acid encodes a ribozyme modified from the group of ribozymes consisting of SEQ ID NO:3, SEQ ID NO:4, SEQ ID NO:5, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID No. 22, wherein the modification consists of an modification selected from the group of modifications consisting of a loop 3 nucleotide substitution, a helix 4 nucleotide substitution, 8 lengthening the helix 4 domain, shortening the helix 4 domain, lengthening the helix 3 domain, shortening the helix 3 domain, shortening the helix 1 domain, lengthening the helix 1 domain, ligation of the ribozyme to a DNA molecule, and conversion of the ribozyme to an RNA phosphothio analog.

14. A method of cleaving an HIV nucleic acid comprising contacting the nucleic acid with a ribozyme encoded by the ribo-endonuclease nucleic acid of claim 1, in vitro.

15. The method of claim 14, wherein the HIV nucleic acid is expressed in a cell.

16. The method of claim 14, wherein the method further comprises the step of transducing a cell with the endo-ribonuclease nucleic acid.

17. A method of inhibiting the expression of an HIV nucleic acid in an isolated cell, comprising transducing the cell with a nucleic acid encoding the endo-ribonuclease nucleic acid of claim 1.

18. The method of claim 17, wherein the cell is isolated from a mammal infected with the HIV virus.

19. The method of claim 17 wherein the cell is a $CD4^+$ cell.

20. The method of claim 17 wherein the cell is a $CD34^+$ hematopoietic stem cell.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: misc_RNA
        ( B ) LOCATION: 1..16
        ( D ) OTHER INFORMATION: /note= "consensus RNA target sequence
            for GUC ribozymes"

( i x ) FEATURE:
        ( A ) NAME/KEY: misc_structure
        ( B ) LOCATION: 1..4
        ( D ) OTHER INFORMATION: /note= "helix 2 structural domain when
            bound to GUC ribozyme"

( i x ) FEATURE:
        ( A ) NAME/KEY: D-loop
        ( B ) LOCATION: 5..8
        ( D ) OTHER INFORMATION: /note= "loop 1 structural domain when
            bound to GUC ribozyme"

( i x ) FEATURE:
        ( A ) NAME/KEY: misc_structure
        ( B ) LOCATION: 9..14
        ( D ) OTHER INFORMATION: /note= "helix 1 structural domain when
            bound to GUC ribozyme"

( x i ) SEQUENCE DESCRIPTION: SEQ ID NO:1:

NNNBNGUCNN NNNNNN                            1 6

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:

(A) NAME/KEY: misc_RNA
(B) LOCATION: 1..16
(D) OTHER INFORMATION: /note= "consensus RNA target sequence for GUA ribozymes"

(ix) FEATURE:
(A) NAME/KEY: misc_structure
(B) LOCATION: 1..4
(D) OTHER INFORMATION: /note= "helix 2 structural domain when bound to GUA ribozyme"

(ix) FEATURE:
(A) NAME/KEY: D-loop
(B) LOCATION: 5..8
(D) OTHER INFORMATION: /note= "loop 1 structural domain when bound to GUA ribozyme"

(ix) FEATURE:
(A) NAME/KEY: misc_structure
(B) LOCATION: 9..14
(D) OTHER INFORMATION: /note= "helix 1 structural domain when bound to GUA ribozyme"

(xi) SEQUENCE DESCRIPTION: SEQ ID NO:2:

NNNNNGUANN NNNNNN 16

(2) INFORMATION FOR SEQ ID NO:3:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..52
(D) OTHER INFORMATION: /note= "pol 3308 GUC ribozyme gene DNA sense strand"

(xi) SEQUENCE DESCRIPTION: SEQ ID NO:3:

ATGTCATTAG AAGTCCACCA GAGAAACACA CGTTGTGGTA TATTACCTGG TA 52

(2) INFORMATION FOR SEQ ID NO:4:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..52
(D) OTHER INFORMATION: /note= "vif 5251 GUC ribozyme gene DNA sense strand"

(xi) SEQUENCE DESCRIPTION: SEQ ID NO:4:

TGTATGCAAG AACCAAACCA GAGAAACACA CGTTGTGGTA TATTACCTGG TA 52

(2) INFORMATION FOR SEQ ID NO:5:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA ( i x ) FEATURE:
    ( A ) NAME/KEY: -
    ( B ) LOCATION: 1..52
    ( D ) OTHER INFORMATION: /note= "env 7931 GUC ribozyme gene DNA
        sense strand"

( x i ) SEQUENCE DESCRIPTION: SEQ ID NO:5:

ATGCCCCAAG AAGTGAACCA GAGAAACACA CGTTGTGGTA TATTACCTGG TA    52

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for pol-2
            ribozyme 3308 target site"

( x i ) SEQUENCE DESCRIPTION: SEQ ID NO:6:

GGACUGUCAA UGACAU    16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for vif
            ribozyme 5251 target site"

( x i ) SEQUENCE DESCRIPTION: SEQ ID NO:7:

UUGGGGUCUG CAUACA    16

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for env-2
            ribozyme 7931 target site"

( x i ) SEQUENCE DESCRIPTION: SEQ ID NO:8:

UCACAGUCUG GGGCAU    16

( 2 ) INFORMATION FOR SEQ ID NO:9:

( i ) SEQUENCE CHARACTERISTICS:
        ( A ) LENGTH: 54 base pairs
        ( B ) TYPE: nucleic acid
        ( C ) STRANDEDNESS: single ( D ) TOPOLOGY: linear ( i i ) MOLECULE TYPE: DNA ( i x ) FEATURE:
    ( A ) NAME/KEY: -
    ( B ) LOCATION: 1..54
    ( D ) OTHER INFORMATION: /note= "anti-2345 GUA ribozyme gene DNA
        sense strand based on the negative
        strand satellite RNA of the Arabis
        Mosaic Virus (AMV)"

( x i ) SEQUENCE DESCRIPTION: SEQ ID NO:9:

TCTTCTAACG AAGTATAACG GCGAAACACA CCTTGTGTGG TATATTACCC GTTG    54

( 2 ) INFORMATION FOR SEQ ID NO:10:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-2425 GUA ribozyme gene DNA
            sense strand based on the negative
            strand satellite RNA of the Arabis
            Mosaic Virus (AMV)"

( x i ) SEQUENCE DESCRIPTION: SEQ ID NO:10:

TCTGATCACG AAGTCTAACG GCGAAACACA CCTTGTGTGG TATATTACCC GTTG    54

( 2 ) INFORMATION FOR SEQ ID NO:11:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-2480 GUA ribozyme gene DNA
            sense strand based on the negative
            strand satellite RNA of the Arabis
            Mosaic Virus (AMV)"

( x i ) SEQUENCE DESCRIPTION: SEQ ID NO:11:

GTAGGTCCCG AAAATAAACG GCGAAACACA CCTTGTGTGG TATATTACCC GTTG    54

( 2 ) INFORMATION FOR SEQ ID NO:12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-4154 GUA ribozyme gene DNA
            sense strand based on the negative
            strand satellite RNA of the Arabis
            Mosaic Virus (AMV)"

( x i ) SEQUENCE DESCRIPTION: SEQ ID NO:12:

TGTGCTGGCG AACATGAACG GCGAAACACA CCTTGTGTGG TATATTACCC GTTG    54

( 2 ) INFORMATION FOR SEQ ID NO:13:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-5331 GUA ribozyme gene DNA sense strand based on the negative strand satellite RNA of the Arabis Mosaic Virus (AMV)"

( x i ) SEQUENCE DESCRIPTION: SEQ ID NO:13:

TCAGGGTCCG AATGTGAACG GCGAAACACA CCTTGTGTGG TATATTACCC GTTG 54

( 2 ) INFORMATION FOR SEQ ID NO:14:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: -
( B ) LOCATION: 1..54
( D ) OTHER INFORMATION: /note= "anti-6581 GUA ribozyme gene DNA sense strand based on the negative strand satellite RNA of the Arabis Mosaic Virus (AMV)"

( x i ) SEQUENCE DESCRIPTION: SEQ ID NO:14:

GTTAATTTCG AACATGAACG GCGAAACACA CCTTGTGTGG TATATTACCC GTTG 54

( 2 ) INFORMATION FOR SEQ ID NO:15:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: -
( B ) LOCATION: 1..54
( D ) OTHER INFORMATION: /note= "anti-6963 GUA ribozyme gene DNA sense strand based on the negative strand satellite RNA of the Arabis Mosaic Virus (AMV)"

( x i ) SEQUENCE DESCRIPTION: SEQ ID NO:15:

TCCATGTGCG AATTGTAACG GCGAAACACA CCTTGTGTGG TATATTACCC GTTG 54

( 2 ) INFORMATION FOR SEQ ID NO:16:

( i ) SEQUENCE CHARACTERISTICS:
( A ) LENGTH: 54 base pairs
( B ) TYPE: nucleic acid (C) STRANDEDNESS: single
(D) TOPOLOGY: linear (ii) MOLECULE TYPE: DNA (ix) FEATURE:
(A) NAME/KEY: -
(B) LOCATION: 1..54
(D) OTHER INFORMATION: /note= "anti-2345 GUA ribozyme gene DNA
sense strand based on the negative
strand satellite RNA of the Chicory
Mosaic Virus (CMV)"

(xi) SEQUENCE DESCRIPTION: SEQ ID NO:16:

TCTTCTAACG AAGTATGCCA GGGAAACACA CCATGTGTGG TATATTATCT GGCA    54

(2) INFORMATION FOR SEQ ID NO:17:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..54
(D) OTHER INFORMATION: /note= "anti-2425 GUA ribozyme gene DNA
sense strand based on the negative
strand satellite RNA of the Chicory
Mosaic Virus (CMV)"

(xi) SEQUENCE DESCRIPTION: SEQ ID NO:17:

TCTGATCACG AAGTCTGCCA GGGAAACACA CCATGTGTGG TATATTATCT GGCA    54

(2) INFORMATION FOR SEQ ID NO:18:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..54
(D) OTHER INFORMATION: /note= "anti-2480 GUA ribozyme gene DNA
sense strand based on the negative
strand satellite RNA of the Chicory
Mosaic Virus (CMV)"

(xi) SEQUENCE DESCRIPTION: SEQ ID NO:18:

GTAGGTCCCG AAAATAGCCA GGGAAACACA CCATGTGTGG TATATTATCT GGCA    54

(2) INFORMATION FOR SEQ ID NO:19:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..54
(D) OTHER INFORMATION: /note= "anti-4154 GUA ribozyme gene DNA
sense strand based on the negative
strand satellite RNA of the Chicory Mosaic Virus (CMV)"

( x i ) SEQUENCE DESCRIPTION: SEQ ID NO:19:

TGTGCTGGCG AACATGGCCA GGGAAACACA CCATGTGTGG TATATTATCT GGCA  54

( 2 ) INFORMATION FOR SEQ ID NO:20:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-5331 GUA ribozyme gene DNA
            sense strand based on the negative
            strand satellite RNA of the Chicory
            Mosaic Virus (CMV)"

( x i ) SEQUENCE DESCRIPTION: SEQ ID NO:20:

TCAGGGTCCG AATGTGGCCA GGGAAACACA CCATGTGTGG TATATTATCT GGCA  54

( 2 ) INFORMATION FOR SEQ ID NO:21:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-6581 GUA ribozyme gene DNA
            sense strand based on the negative
            strand satellite RNA of the Chicory
            Mosaic Virus (CMV)"

( x i ) SEQUENCE DESCRIPTION: SEQ ID NO:21:

GTTAATTTCG AACATGGCCA GGGAAACACA CCATGTGTGG TATATTATCT GGCA  54

( 2 ) INFORMATION FOR SEQ ID NO:22:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..54
        ( D ) OTHER INFORMATION: /note= "anti-6963 GUA ribozyme gene DNA
            sense strand based on the negative
            strand satellite RNA of the Chicory
            Mosaic Virus (CMV)"

( x i ) SEQUENCE DESCRIPTION: SEQ ID NO:22:

TCCATGTGCG AATTGTGCCA GGGAAACACA CCATGTGTGG TATATTATCT GGCA  54

( 2 ) INFORMATION FOR SEQ ID NO:23:

( i ) SEQUENCE CHARACTERISTICS:
        ( A ) LENGTH: 16 base pairs ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for
            anti-2345 GUA ribozyme target site"

( x i ) SEQUENCE DESCRIPTION: SEQ ID NO:23:

AUACAGUAUU AGAAGA 16

( 2 ) INFORMATION FOR SEQ ID NO:24:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for
            anti-2425 GUA ribozyme target site"

( x i ) SEQUENCE DESCRIPTION: SEQ ID NO:24:

AGACAGUAUG AUCAGA 16

( 2 ) INFORMATION FOR SEQ ID NO:25:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for
            anti-2480 GUA ribozyme target site"

( x i ) SEQUENCE DESCRIPTION: SEQ ID NO:25:

UAUUAGUAGG ACCUAC 16

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: -
        ( B ) LOCATION: 1..16
        ( D ) OTHER INFORMATION: /note= "HIV target sequence for
            anti-4154 GUA ribozyme target site"

( x i ) SEQUENCE DESCRIPTION: SEQ ID NO:26:

CAUGGGUACC AGCACA 16

(2) INFORMATION FOR SEQ ID NO:27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

(ix) FEATURE:
        (A) NAME/KEY: -
        (B) LOCATION: 1..16
        (D) OTHER INFORMATION: /note= "HIV target sequence for
            anti-5331 GUA ribozyme target site"

(xi) SEQUENCE DESCRIPTION: SEQ ID NO:27:

CACAAGUAGA CCCUGA                                               16

(2) INFORMATION FOR SEQ ID NO:28:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

(ix) FEATURE:
        (A) NAME/KEY: -
        (B) LOCATION: 1..16
        (D) OTHER INFORMATION: /note= "HIV target sequence for
            anti-6581 GUA ribozyme target site"

(xi) SEQUENCE DESCRIPTION: SEQ ID NO:28:

CAUGUGUAAA AUUAAC                                               16

(2) INFORMATION FOR SEQ ID NO:29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

(ix) FEATURE:
        (A) NAME/KEY: -
        (B) LOCATION: 1..16
        (D) OTHER INFORMATION: /note= "HIV target sequence for
            anti-6963 GUA ribozyme target site"

(xi) SEQUENCE DESCRIPTION: SEQ ID NO:29:

ACAAUGUACA CAUGGA                                               16

(2) INFORMATION FOR SEQ ID NO:30:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: misc_RNA
        (B) LOCATION: 1..14
        (D) OTHER INFORMATION: /note= "consensus RNA target sequence
            for GUC ribozymes"

(ix) FEATURE:

( A ) NAME/KEY: misc_structure
                    ( B ) LOCATION: 1..4
                    ( D ) OTHER INFORMATION: /note= "helix 2 structural domain when
                          bound to GUC ribozyme"

( i x ) FEATURE:
                    ( A ) NAME/KEY: D-loop
                    ( B ) LOCATION: 5..8
                    ( D ) OTHER INFORMATION: /note= "loop 5 structural domain when
                          bound to GUC ribozyme"

( i x ) FEATURE:
                    ( A ) NAME/KEY: misc_structure
                    ( B ) LOCATION: 9..14
                    ( D ) OTHER INFORMATION: /note= "helix 1 structural domain when
                          bound to GUC ribozyme"

( x i ) SEQUENCE DESCRIPTION: SEQ ID NO:30:

NNNBNGUCNN NNNN                                                                        14

( 2 ) INFORMATION FOR SEQ ID NO:31:

( i ) SEQUENCE CHARACTERISTICS:
                    ( A ) LENGTH: 50 base pairs
                    ( B ) TYPE: nucleic acid
                    ( C ) STRANDEDNESS: single
                    ( D ) TOPOLOGY: linear ( i i ) MOLECULE TYPE: RNA ( i x ) FEATURE:
                    ( A ) NAME/KEY: misc_RNA
                    ( B ) LOCATION: 1..50
                    ( D ) OTHER INFORMATION: /note= "GUC ribozyme prototype"

( i x ) FEATURE:
                    ( A ) NAME/KEY: misc_structure
                    ( B ) LOCATION: 1..6
                    ( D ) OTHER INFORMATION: /note= "helix 1 structural domain when
                          bound to consensus RNA target sequence
                          for GUC ribozymes"

( i x ) FEATURE:
                    ( A ) NAME/KEY: D-loop
                    ( B ) LOCATION: 7..10
                    ( D ) OTHER INFORMATION: /note= "loop 1 structural domain when
                          bound to consensus RNA target sequence
                          for GUC ribozymes"

( i x ) FEATURE:
                    ( A ) NAME/KEY: misc_structure
                    ( B ) LOCATION: 11..14
                    ( D ) OTHER INFORMATION: /note= "helix 2 structural domain when
                          bound to consensus RNA target sequence
                          for GUC ribozymes"

( i x ) FEATURE:
                    ( A ) NAME/KEY: misc_structure
                    ( B ) LOCATION: 16..19
                    ( D ) OTHER INFORMATION: /note= "helix 3 structural domain"

( i x ) FEATURE:
                    ( A ) NAME/KEY: D-loop
                    ( B ) LOCATION: 20..26
                    ( D ) OTHER INFORMATION: /note= "loop 2 structural domain"

( i x ) FEATURE:
                    ( A ) NAME/KEY: misc_structure
                    ( B ) LOCATION: 27..29
                    ( D ) OTHER INFORMATION: /note= "helix 4 structural domain"

( i x ) FEATURE:
                    ( A ) NAME/KEY: D-loop
                    ( B ) LOCATION: 30..32
                    ( D ) OTHER INFORMATION: /note= "loop 3 hair-pin structural
                          domain"

( i x ) FEATURE:

(A) NAME/KEY: misc_structure
(B) LOCATION: 33..35
(D) OTHER INFORMATION: /note= "helix 4 structural domain"

(ix) FEATURE:
(A) NAME/KEY: D-loop
(B) LOCATION: 36..44
(D) OTHER INFORMATION: /note= "loop 4 structural domain"

(ix) FEATURE:
(A) NAME/KEY: misc_structure
(B) LOCATION: 45..48
(D) OTHER INFORMATION: /note= "helix 3 structural domain"

(xi) SEQUENCE DESCRIPTION: SEQ ID NO:31:

NNNNNNAGAA VNNNACCAGA GAAACACACG UUGUGGUAUA UUACCUGGUA 50

(2) INFORMATION FOR SEQ ID NO:32:

(i) SEQUENCE CHARACTERISTICS:
(A) LENGTH: 59 base pairs
(B) TYPE: nucleic acid
(C) STRANDEDNESS: single
(D) TOPOLOGY: linear (ii) MOLECULE TYPE: RNA (ix) FEATURE:
(A) NAME/KEY: misc_RNA
(B) LOCATION: 1..59
(D) OTHER INFORMATION: /note= "GUC ribozyme prototype with
loop 3 and helix 4 modifications"

(ix) FEATURE:
(A) NAME/KEY: misc_structure
(B) LOCATION: 1..6
(D) OTHER INFORMATION: /note= "helix 1 structural domain when
bound to consensus RNA target sequence
for GUC ribozymes"

(ix) FEATURE:
(A) NAME/KEY: D-loop
(B) LOCATION: 7..10
(D) OTHER INFORMATION: /note= "loop 1 structural domain when
bound to consensus RNA target sequence
for GUC ribozymes"

(ix) FEATURE:
(A) NAME/KEY: misc_structure
(B) LOCATION: 11..14
(D) OTHER INFORMATION: /note= "helix 2 structural domain when
bound to consensus RNA target sequence
for GUC ribozymes"

(ix) FEATURE:
(A) NAME/KEY: misc_structure
(B) LOCATION: 16..19
(D) OTHER INFORMATION: /note= "helix 3 structural domain"

(ix) FEATURE:
(A) NAME/KEY: D-loop
(B) LOCATION: 20..26
(D) OTHER INFORMATION: /note= "loop 2 structural domain"

(ix) FEATURE:
(A) NAME/KEY: misc_structure
(B) LOCATION: 27..33
(D) OTHER INFORMATION: /note= "helix 4 structural domain
modification of prototype GUC ribozyme"

(ix) FEATURE:
(A) NAME/KEY: D-loop
(B) LOCATION: 34..37
(D) OTHER INFORMATION: /note= "loop 3 hair-pin (tetraloop)
structural domain modification of
prototype GUC ribozyme"

(ix) FEATURE:

(A) NAME/KEY: misc_structure
(B) LOCATION: 38..44
(D) OTHER INFORMATION: /note= "helix 4 structural domain modification of prototype GUC ribozyme"

(ix) FEATURE:
(A) NAME/KEY: D-loop
(B) LOCATION: 45..53
(D) OTHER INFORMATION: /note= "loop 4 structural domain"

(ix) FEATURE:

( i x ) FEATURE:
                ( A ) NAME/KEY: D-loop
                ( B ) LOCATION: 7..10
                ( D ) OTHER INFORMATION: /note= "loop 1 structural domain when
                        bound to consensus RNA target sequence
                        for GUA ribozymes"

( i x ) FEATURE:
                ( A ) NAME/KEY: misc_structure
                ( B ) LOCATION: 11..14
                ( D ) OTHER INFORMATION: /note= "helix 2 structural domain when
                        bound to consensus RNA target sequence
                        for GUA ribozymes"

( i x ) FEATURE:
                ( A ) NAME/KEY: misc_structure
                ( B ) LOCATION: 16..19
                ( D ) OTHER INFORMATION: /note= "helix 3 structural domain"

( i x ) FEATURE:
                ( A ) NAME/KEY: D-loop
                ( B ) LOCATION: 20..26
                ( D ) OTHER INFORMATION: /note= "loop 2 structural domain"

( i x ) FEATURE:
                ( A ) NAME/KEY: misc_structure
                ( B ) LOCATION: 27..29
                ( D ) OTHER INFORMATION: /note= "helix 4 structural domain"

( i x ) FEATURE:
                ( A ) NAME/KEY: D-loop
                ( B ) LOCATION: 30..34
                ( D ) OTHER INFORMATION: /note= "loop 3 hair-pin structural
                        domain"

( i x ) FEATURE:
                ( A ) NAME/KEY: misc_structure
                ( B ) LOCATION: 35..37
                ( D ) OTHER INFORMATION: /note= "helix 4 structural domain"

( i x ) FEATURE:
                ( A ) NAME/KEY: D-loop
                ( B ) LOCATION: 38..46
                ( D ) OTHER INFORMATION: /note= "loop 2 structural domain"

( i x ) FEATURE:
                ( A ) NAME/KEY: misc_structure
                ( B ) LOCATION: 47..50
                ( D ) OTHER INFORMATION: /note= "helix 3 structural domain"

( x i ) SEQUENCE DESCRIPTION: SEQ ID NO:34:

NNNNNNCGAA NNNNGCCAGG GAAACACACC AUGUGUGGUA UAUUAUCUGG CA                52

( 2 ) INFORMATION FOR SEQ ID NO:35:

( i ) SEQUENCE CHARACTERISTICS:
                ( A ) LENGTH: 52 base pairs
                ( B ) TYPE: nucleic acid
                ( C ) STRANDEDNESS: single
                ( D ) TOPOLOGY: linear ( i i ) MOLECULE TYPE: RNA ( i x ) FEATURE:
                ( A ) NAME/KEY: misc_RNA
                ( B ) LOCATION: 1..52
                ( D ) OTHER INFORMATION: /note= "negative strand satellite RNA
                        of Arabis Mosaic Virus-based GUA ribozyme"

( i x ) FEATURE:
                ( A ) NAME/KEY: misc_structure
                ( B ) LOCATION: 1..6
                ( D ) OTHER INFORMATION: /note= "helix 1 structural domain when
                        bound to consensus RNA target sequence
                        for GUA ribozymes"

(ix) FEATURE:
(A) NAME/KEY: D-loop
(B) LOCATION: 7..10
(D) OTHER INFORMATION: /note= "loop 1 structural domain when bound to consensus RNA target sequence for GUA ribozymes"

(ix) FEATURE:
(A) NAME/KEY: misc_structure
(B) LOCATION: 11..14
(D) OTHER INFORMATION: /note= "helix 2 structural domain when bound to consensus RNA target sequence for GUA ribozymes"

(ix) FEATURE:
(A) NAME/KEY: misc_structure
(B) LOCATION: 16..19
(D) OTHER INFORMATION: /note= "helix 3 structural domain"

(ix) FEATURE:
(A) NAME/KEY: D-loop
(B) LOCATION: 20..26
(D) OTHER INFORMATION: /note= "loop 2 structural domain"

(ix) FEATURE:
(A) NAME/KEY: misc_structure
(B) LOCATION: 27..29
(D) OTHER INFORMATION: /note= "helix 4 structural domain"

(ix) FEATURE:
(A) NAME/KEY: D-loop
(B) LOCATION: 30..34
(D) OTHER INFORMATION: /note= "loop 3 hair-pin structural domain"

(ix) FEATURE:
(A) NAME/KEY: misc_structure
(B) LOCATION: 35..37
(D) OTHER INFORMATION: /note= "helix 4 structural domain"

(ix) FEATURE:
(A) NAME/KEY: D-loop
(B) LOCATION: 38..46
(D) OTHER INFORMATION: /note= "loop 4 structural domain"

(ix) FEATURE:
(A) NAME/KEY: misc_structure
(B) LOCATION: 47..50
(D) OTHER INFORMATION: /note= "helix 3 structural domain"

(xi) SEQUENCE DESCRIPTION: SEQ ID NO:35:

NNNNNNCGAA NNNNAACGGC GAAACACACC UUGUGUGGUA UAUUACCCGU UG        52